Figure 1:
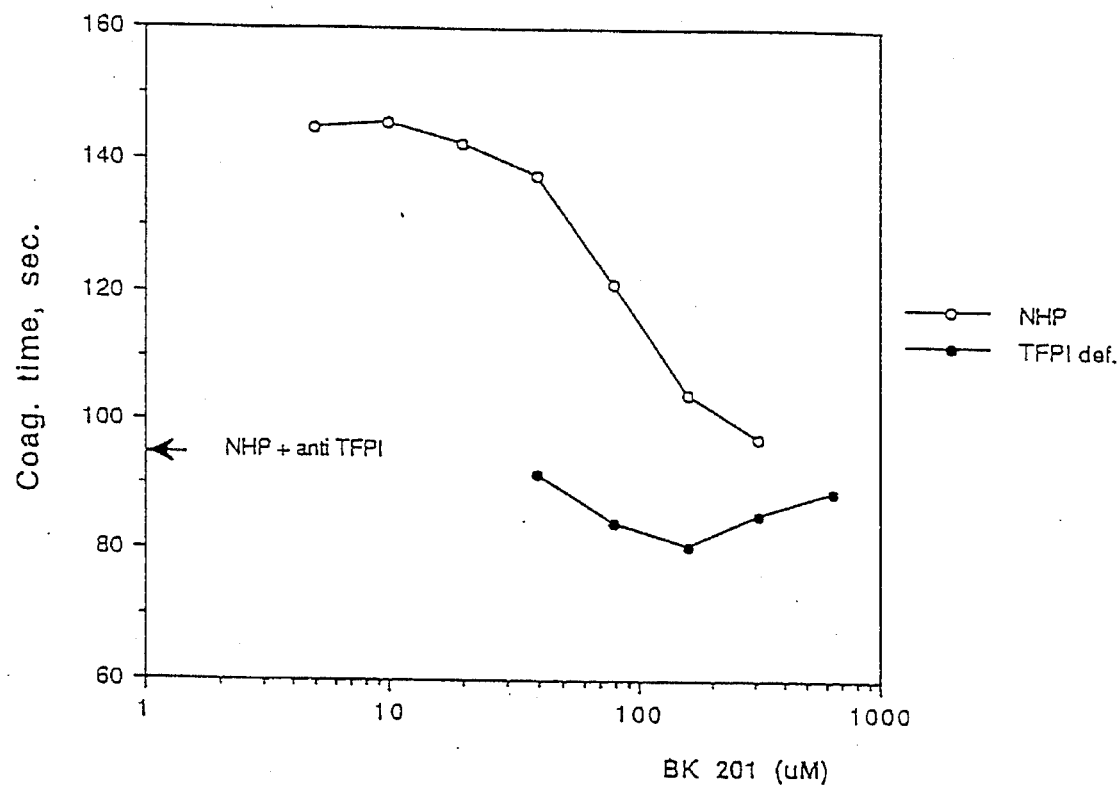

United States Patent [19]

Worsaae et al.

[11] Patent Number: 5,622,988
[45] Date of Patent: Apr. 22, 1997

[54] USE OF A LOW MOLECULAR WEIGHT METABOLITE FROM FUNGUS FOR REDUCING PROLONGED COAGULATION TIME

[75] Inventors: Helle Worsaae, Gentofte; Frank W. Rasmussen, Valby; Mirella E. Rasmussen, Copenhagen, all of Denmark

[73] Assignee: Novo Nordisk A/S, Bagsvaerd, Denmark

[21] Appl. No.: 405,336

[22] Filed: Mar. 16, 1995

Related U.S. Application Data

[63] Continuation-in-part of Ser. No. 95,785, Jul. 22, 1993, Pat. No. 5,409,951, which is a continuation-in-part of Ser. No. 714,107, Jun. 11, 1991, abandoned.

[30] Foreign Application Priority Data

Jun. 15, 1990 [DK] Denmark .................. 1461/90

[51] Int. Cl.⁶ .................................................. A61K 31/35
[52] U.S. Cl. ............................................................ 514/455
[58] Field of Search .............................. 514/455; 549/392

[56] References Cited

FOREIGN PATENT DOCUMENTS 0507039  10/1992  European Pat. Off. .

OTHER PUBLICATIONS

Chemical Abstracts, vol. 99, No. 15, The Abstract No. 118903u (1983).
Chemical Abstracts, vol. 91, No. 24, The Abstract No. 198935d (1979).
Patent Abstracts of Japan, vol. 10, No. 85, C–336, Abstract of JP, A, 60–218382 (1985).

*Primary Examiner*—Nicky Chan
*Attorney, Agent, or Firm*—Zelson T. Zelson, Esq.; Cheryl H. Agris, Esq.

[57] ABSTRACT

The present invention relates to the use of compounds of formula I

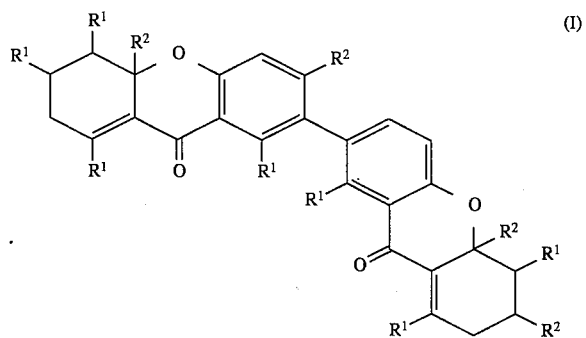

wherein $R^1$ is independently hydrogen, hydroxy, alkyl with 1 to 6 carbon atoms, acyloxy groups with 1 to 6 carbon atoms, alkyloxy with 1 to 6 carbon atoms or from 1 to 5 sugar moieties; and $R^2$ is independently hydrogen, or alkyl with 1 to 6 carbon atoms, in the reduction of coagulation time in mammals.

2 Claims, 3 Drawing Sheets

USE OF A LOW MOLECULAR WEIGHT METABOLITE FROM FUNGUS FOR REDUCING PROLONGED COAGULATION TIME

This application is a continuation-in-part of U.S. Ser. No. 08/095,785 filed Jul. 22, 1993, now U.S. Pat. No. 5,409,951, and which is a continuation-in-part of U.S. Ser. No. 07/714,107 filed Jun. 11, 1991 now abandoned. The contents of Ser. No. 08/095,785 are incorporated herein by reference in their entirety.

FIELD OF THE INVENTION

This invention relates to a novel use of a low molecular weight metabolite from the mold genus Ascochyta. This compound is useful in the treatment of medical conditions which are characterized by prolonged coagulation time.

BACKGROUND OF THE INVENTION

It has been known for some time that some species of the genus Ascochyta produce different metabolites exhibiting biological activity, in particular as phytotoxins. Examples thereof are e.g. an isoqinoline alkaloid, chrysantone, isolated from *Ascochyta chrysanthemi* (*Phytochemistry,* 28(3): 923–927, 1989), which is a phytotoxin, and which also exhibits antibacterial and weak antifungal activity. Ascotoxin (Decumbin) produced by *A. imperfecta* (Y. Suzuki, H. Tanake, H. Aoki and T. Tamura, *Agric. Biol. Chem.* 1970, 34, 395), is a strong plant pathogen with a phytotoxic activity exhibiting a strong inhibition of the growth of lucerne and rape. Cytochalasin A and B produced by *A. heteromorpha* (*J. Natural Products,* 50 (5): 989–998, 1987) are well known myco- and phytotoxins belonging to the cytochalasins a class of mold metabolites exhibiting various biological effects.

Ascochyta metabolites having the general formula (I)

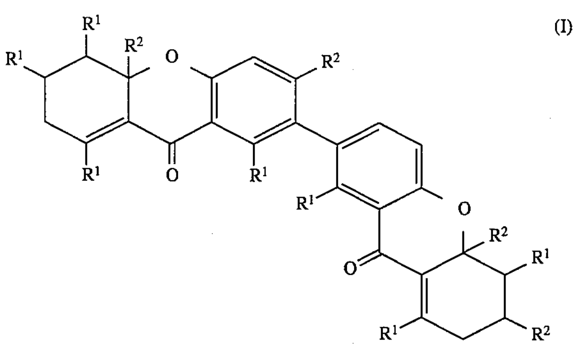

(I)

wherein $R^1$ is independently hydrogen, hydroxy, alkyl with 1 to 6 carbon atoms, acyloxy groups with 1 to 6 carbon atoms, alkyloxy with 1 to 6 carbon atoms, or from 1 to 5 sugar moieties; and $R^2$ is independently hydrogen, or alkyl with 1 to 6 carbon atoms, has been described in U.S. Ser. No. 08/095,785, the contents of which are incorporated herein by reference. These compounds are disclosed as exhibiting strong antifungal activity without phytotoxic activity, and are proposed for use in treatment of fungal plant diseases. It has now been determined, however, that compounds of this general formula also have a pharmaceutical utility, in that they show activity in inhibiting Tissue Factor Pathway Inhibitor(TFPI), and therefore can be used in reducing coagulation time in medical conditions which are characterized by excess or uncontrolled bleeding.

SUMMARY OF THE INVENTION

The present invention relates to a method of decreasing coagulation time in a mammal, comprising administering to the mammal an effective amount of a compound of formula (I) herein. In a preferred embodiment, the compound is a compound (Ia) of formula I, wherein $R^1$ is —OH, and $R^2$ is —$CH_3$. The invention also relates to a pharmaceutical composition comprising a compound of formula (I), in combination with a pharmaceutically acceptable carrier.

The method and composition of the present invention are useful in alleviation of prolonged bleeding tendencies associated with various medical conditions, such as hemophilia, or bleeding associated with surgery. In a preferred embodiment, the mammal receiving the treatment is a human being.

DEPOSIT OF MICROORGANISMS

For the purpose of describing this invention in detail a strain of the fungus *Ascochyta sp.* (CMI CC No. 337158) has been deposited with the Commonwealth Mycological Institute Culture Collection (CMI CC), Ferry Lane, Kew, Surrey TW9 3AF, England, for the purposes of patent procedure on the date indicated below. CMI CC 337158 belongs to the class Deuteromycetes, subclass Coelomycetidae, and family Sphaerioidaceae. The fungus is a new species of the genus Ascochyta which was isolated in 1988 from a leaf of *Panicum maximum.*

BRIEF DESCRIPTION OF THE DRAWING

FIG. 1 shows the effect of a compound of the invention, BK 201, on human plasma and TFPI(EPI)-deficient human plasma.

FIG. 2 shows the effect of BK 201 on clotting time in normal rabbit plasma and FVIII-deficient rabbit plasma.

FIG. 3 shows the molecular structure of BK 201.

DETAILED DESCRIPTION OF THE INVENTION

Coagulation is a complex precess involving many protein factors. The coagulation process can be initiated via the intrinsic pathway through contact with a foreign surface or via the extrinsic pathway through contact with damaged tissue. By extrinsic activation the circulating blood comes in contact with tissue factor(TF). TF is a cofactor for coagulation factor VIII(FVIII) and the TF-FVII/TF-FVIIa complex activates FX and FIX. Due to the activation of FIX, "intrinsic coagulation" is also influenced by TF activation and an increasing amount of evidence indicates that TF-FVII activation is most important for the initiation of the coagulation reaction (Österud and Rapaport, Proc. Nat. Acad Sci. USA 74: 5260, 1977). The coagulation factors of the extrinsic pathway are inhibited by Extrinsic Pathway Inhibitor (EPI), also known as Lipoprotein Associated Coagulation Inhibitor (LACI; Broze and Miletich, Blood 69: 150, 1990) and Tissue Factor Pathway Inhibitor (TFPI; Hoist et al., Thrombosis and Haemostasis 71: 214, 1994). This factor is a Kunitz-type protease inhibitor which binds and inhibits FXa. The EPI-FXa complex inhibits FVIIa-TF (Rapaport, Blood 73: 359, 1989). the significance of EPI for the coagulation reaction has not yet been established since only unphysiologically high concentrations affect conventional coagulation assays(Broze et al., Biochemistry 29: 7539, 1990). Therefore, EPI activity is measured in sophisticated assays where EPI is allowed to bind FXa and the EPI-FXa is added to TF-FVII reactants that may activate FIX or FX(Bajaj et al., J. Clin. Invest. 79: 1974, 1987; Sandset et al., Thromb. Res. 47: 389, 1987).

In normal hemostasis, the coagulation factors are in balance with each other.™ However, in some circumstances excessive bleeding is observed. Examples are hemophilia caused by lack of FVIII or FIX, and idiopathic thrombocytopenia (ITP) caused by reduced platelet counts. Surgery also often causes excessive bleeding. Other agents which have been used to prevent bleeding are FIX, FVIII, FVIIa, aprotinin and tranexamic acid.

It has not previously been shown that a compound of formula I

Figure 2:
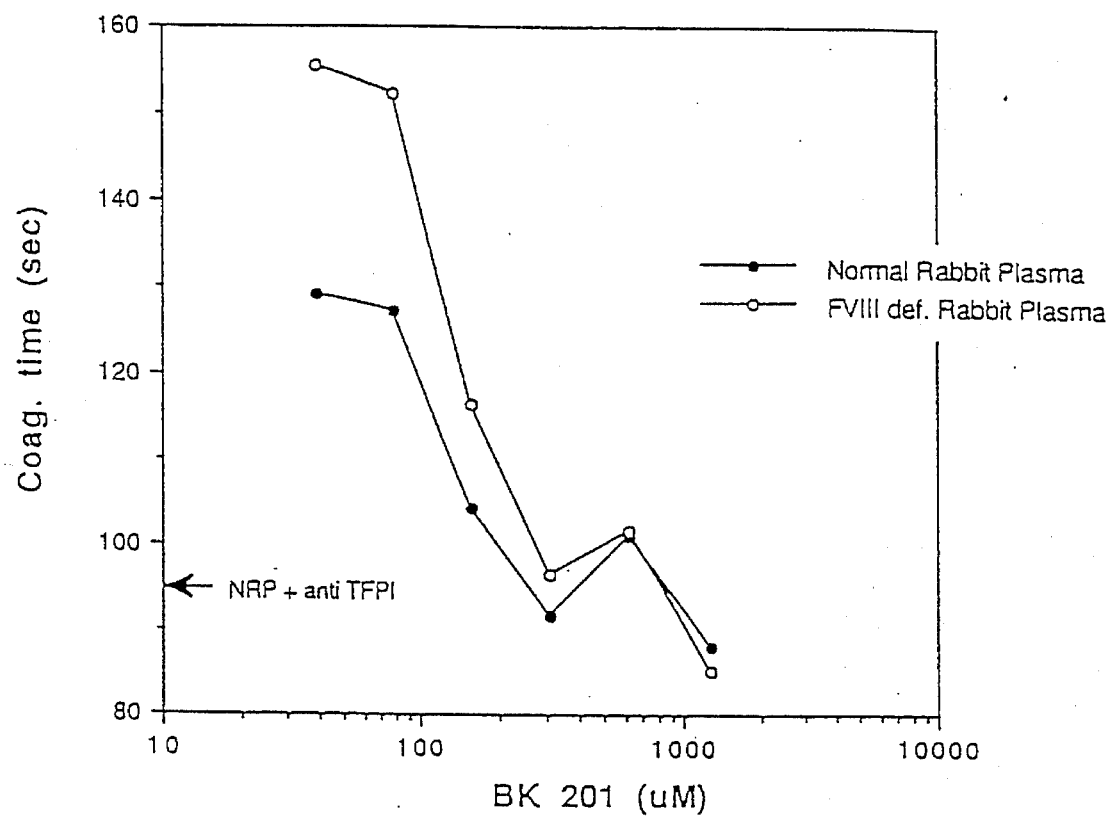

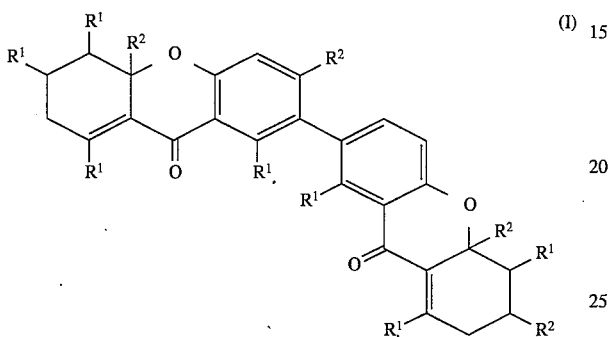

wherein $R^1$ is independently hydrogen, hydroxy, alkyl with 1 to 6 carbon atoms, acyloxy groups with 1 to 6 carbon atoms, alkyloxy with 1 to 6 carbon atoms, or from 1 to 5 sugar moieties; and $R^2$ is independently hydrogen, or alkyl with 1 to 6 carbon atoms, is an inhibitor of EPI activity. The ability to inhibit EPI activity has been shown to be an indicator of the ability to accelerate the coagulation process, as described in copending U.S. Ser. No. 08/050,179, the contents of which are incorporated herein by reference. As described therein, plasma EPI has a significant affect on coagulation time, and thus plays an important role in hemostatic balance. It is further shown therein that blocking of EPI activity aids in reducing bleeding tendencies. The inhibitory capacity of the present compounds is evaluated in vitro in an assay in which coagulation is induced by addition of TF to plasma. Such an assay mimics the physiological condition in that it is the only type of coagulation assay which is dependent on the presence of FVII, FVIII, and FIX, all factors that are necessary to obtain normal hemostasis. Addition of a compound of formula I to plasma in such an assay results in a significant decrease of clotting time, as shown in FIGS. 1 and 2.

In one preferred embodiment the invention relates to use of a compound (Ia) of formula I, wherein $R^1$ is —OH, and $R^2$ is —CH$_3$.

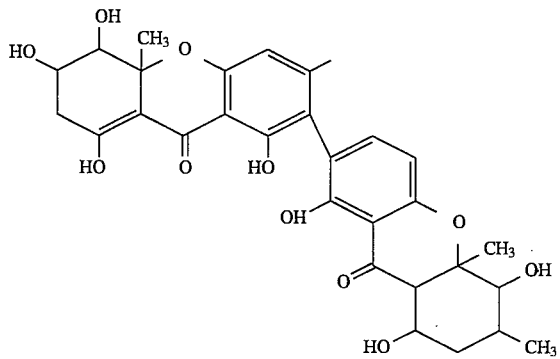

In a more specific embodiment, compound Ia has the stereoconfiguration of

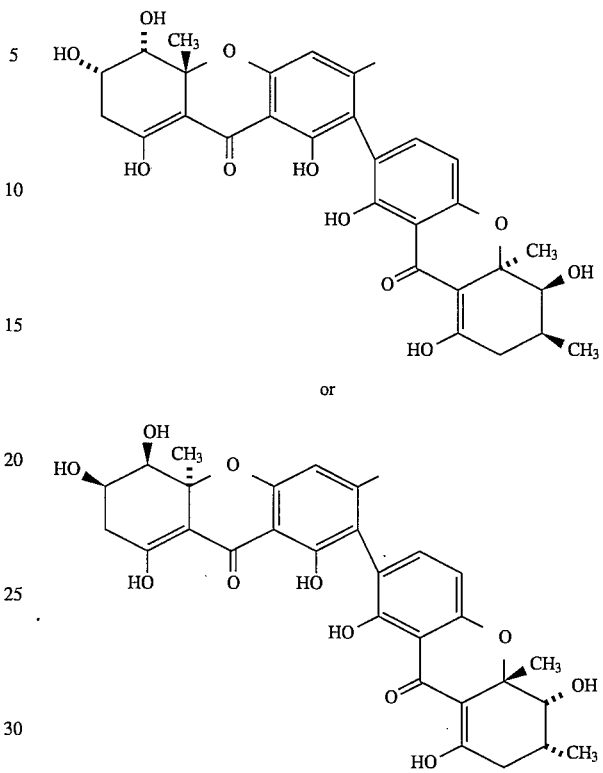

or

The compound of formula Ia is isolatable as a metabolite from a novel species of the genus Ascochyta, *Ascochyta sp.* (CMI CC No. 337158). The compound of formula Ia, also referred to herein as BK201, may be prepared by aerobic cultivation on suitable nutrient media under conditions hereinafter described of a strain of the fungus *Ascochyta sp.* (CMI CC 337158) and thereafter recovering the active component from the fermentation medium.

The natural metabolite may subsequently be modified chemically in order to obtain various derivatives thereof. The derivatives may be produced in order to improve certain properties with the metabolite such as its solubility in aqueous media, its hydrophobicity, hydrophilicity, stability, specificity, etc. It is also contemplated that compounds according to the invention may be produced by well known chemical synthetic processes using available starting materials. One group of derivatives is compounds of formula I, wherein one or several hydroxy groups have been glycosylated. Another group comprises compounds of formula I, wherein one or several hydroxy groups have been acylated. A further group of derivatives is compounds of formula I, wherein one or several hydroxy groups have been alkylated.

Although the invention discussed hereinbelow principally deals with the specific strain CMI CC 337158, it is well known in the art that the properties of microorganisms may be varied naturally and artificially. Thus all strains of *Ascochyta sp.* including variants, recombinants and mutants, whether obtained by natural selection, produced by the action of mutating agents such as ionizing radiation or ultraviolet irradiation, or by the action of chemical mutagens such as nitrosoguanidine, are considered as sources of the compounds useful in the present invention. It is also well known that closely related fungal species within a genus produce related metabolites of the same or similar activity, but with slight differences in chemical structure. The present invention therefore is meant to encompass such closely related compounds.

The present compounds can be used to treat any conditions in which excessive or uncontrolled bleeding is a symptom of the condition. Examples of such conditions include hemophilia A and B, disseminated intravascular coagulation(DIC), idiopathic thrombocytopenia(ITP), and excessive bleeding associated with surgery. The individual to be treated may be any mammal, and is preferably a human being. The amount of compound administered will vary according to the extent of the bleeding and the method of administration. Administration may be oral or parenteral, and when parenteral, is preferably intravenous. Generally, the dosage range of the compound for a small mammal, such as a rabbit, is 15–50 μmoles per kg of body weight; for larger mammals, such as humans, 5–50 μmoles, preferably about 10–20 μmoles, per kg of body weight, is useful. This corresponds to about 2–25 mg/kg body weight.

For ease of administration, the compound will typically be combined with a pharmaceutically acceptable carrier. Such carriers include water, physiological saline, ethanol, polyols, e.g., glycerol or propylene glycol, or vegetable oils. As used herein. "pharmaceutically acceptable carriers" also encompasses any and all solvents. dispersion media, coatings, antifungal agents, preservatives, isotonic agents and the like. Except insofar as any conventional medium is incompatible with the active ingredient and its intended use, its use in the compositions of the present invention is contemplated.

A strain of *Ascochyta sp.* from which the preferred compound is obtainable has the following characteristics:

Description of the Strain

Colony: On potato carrot agar greyish sepia to isabelline; reverse sepia.

Mycelium; Sparse to abundant, composed of yellowish brown to light brown, branched, septate hyphae 2–3.5 μm wide, with chiefly smooth, but sometimes roughened walls.

Conidiomata: Pycnidial, partially immersed in the agar, solitary, yellowish brown to dark brick, unilocular, subglobose with short necks, 160–180 μm wide, overall height 180–200 μm, ostiolate. Conidiomatal (pycnidial) wall pseudoparenchymatic, composed of 4–7 cell layers (textura angularis); the outer cell layers brown to dark brick, thick-walled, the innermost layer lining the pycnidial cavity yellowish to hyaline.
- Ostioles: Circular 15–20 μm wide, surrounded by cells darker than the pycnidial wall.
- Conidiogenous Cells: Hyaline, subglobose to ampulliform, phialidic, with periclinal thickening, arising from the innermost layer of cells lining the pycnidial cavity.
- Conidia: Yellowish brown to pale brown, cylindrical to ellipsoid, apex rounded, base truncate or rounded (6.5–9)μm ×(2–3)μm, >93% medianly 1-septate, <7% 2–3 septate.

CMI CC 337158 is a new species in the genus Ascochyta. It belongs to the section Ascochytella. It is closely related to *A. zeicola* Ellis & Everhart, but differs in having a small percentage of 2–3 septate conidia. With age some pycnidia produce >70% 2–3 septate conidia.

EXAMPLES

Cultivation of Strain

The fungus may be grown on agar slants containing the following ingredients in grams/liter:

| | |
|---|---|
| yeast extract | 4.0 |
| potassium dihydrogen phosphate | 1.0 |
| magnesium sulphate heptahydrate | 0.1 |
| glucose | 15 |
| Bacto ® (Difco Laboratories, Detroit, USA) agar | 20 |

This substrate is autoclaved at 121° C. for 20 or 40 minutes and will, hereinafter, be referred to as YPG agar. Slants contain 12 ml YPG agar and after inoculation they are incubated at 20°–25° C. for 7 days or longer.

BK201 Production

A substrate for shake flasks was prepared using tap water with the following ingredients in grams per liter:

| | |
|---|---|
| maltodextrin-Glucidex ® 6 | 90 |
| ammonium sulphate | 1.0 |
| corn steep liquor | 25 |
| potassium dihydrogen phosphate | 0.5 |

The pH is adjusted to 4.5 before the substrate is sterilized at 121° C. for 40 minutes. A 500 ml Erlenmeyer flask with 100 ml of substrate was inoculated with $10^6$ spores from a YPG agar slant previously inoculated with CMI CC 337158. The flasks were shaken at 230 rpm at 25° C. for 3–7 days whereafter the fermentation broth was centrifuged. The supernatant containing the BK201 was thereby separated from the mycelium. The mycelium was discarded and the supernatant was analyzed for fungicidal activity, which is the original activity ascribed to the compound. The supernatant is also analyzable for anti-EPI activity to identify the presence of BK201.

The compound can also be produced in surface cultures in accordance with well known procedures.

The fermentation can also be carried out in media containing other sources of carbon and nitrogen assimilable by the microorganism and generally low levels of inorganic salts. In addition, the media may be supplemented with trace metals, although if complex sources of carbon and nitrogen are employed, they are usually present in the complex sources.

Extraction of the Active Compound

The compound of formula Ia of this invention can be extracted from the culture broth as follows:

9.65 liters of culture broth were filtered after addition of 80 g High Flow Supercell (filter aid), whereby 5.4 l of filtrate was obtained. The mycelium was then resuspended in 3 l of water, and filtered once more to obtain 3.5 l filtrate. The filtrate was then filtered on Supra 50 filters from Seitz (Germany). This filtrate was concentrated by vacuum evaporation at 20° C., to 1 liter.

To remove impurities from the concentrate 1000 ml ethanol was added. After mixing for 15 minutes the precipitate was filtered off. The filtrate was then concentrated to 800 ml by vacuum evaporation at 20° C. The pH of this concentrate was adjusted to 3.0 and then 800 ml ethylacetate was added. This mixture was shaken for 5 minutes in a separating funnel and then left for 15 minutes to separate into 2 phases.

The upper phase (ethylacetate) was placed in a deep freezer over night, in order to freeze out the water, which the next day was quickly filtered off on a fiberglass filter GF/F (Whatman). The waterfree filtrate was then concentrated by vacuum evaporation at 20° C. to 100 ml.

The lower phase was extracted once more with one volume of ethylacetate. The ethylacetate phase from this extraction was treated as mentioned above. After concentration it was mixed with the first ethylacetate concentrate, and then further concentrated to 50 ml by vacuum evaporation.

The 50 ml concentrate was placed in a separating funnel with 300 ml acetonitrile and was then extracted with 2×500 ml hexane. After extraction 370 ml acetonitrile phase was concentrated to about 100 ml and was then left overnight in the refrigerator to crystallize.

The crystals were isolated and dissolved in a small amount of acetonitrile filtered on a 0.45 μm membrane filter and then placed at room temperature to crystallize for 3–4 hours. The crystals were separated from the mother liquid and dried after rinsing with a small amount of acetonitrile.

The mother liquid was further concentrated and another crystallization was made. This was continued until no further crystallization took place. The amount of crystals obtained was about 800 mg, corresponding to a recovery of one third of the activity found in the culture broth.

Analysis—HPLC Method

Column: Nucleosil $C_{18}$ 4.6×120 mm

Flow: 1 ml/min

Eluent: 48% acetonitrile in deionized water+0.05% trifluor acetic acid

Detector: 280 nm

Retention time about 10 minutes

Structure determination of 5,5',6,6',7,7'-Hexahydro-1,1',5,5',6,8,8' heptahydroxy-3,6',10a,10a'-tetramethyl-9,9'-dioxo-[2,2'-bixanthene]

The structure was determined using X-ray crystallography on crystals achieved from recrystallization from acetonitrile. The structure was confirmed by the $^1H$ and $^{13}C$ NMR and mass spectroscopic determinations.

Crystallographic Data

Unit cell dimensions and reflection intensities were measured on an Enraf-Nonius CAD-4 diffractometer with graphite monochromated MoK γ-radiation. Due to the rather small crystal size data were collected at low temperature. The structure was determined using the SHELX-76 (G. M. Sheldrick. SHELX-76. Program for crystal structure determination. University of Cambridge, England, 1976) and SHELX-86 (G. M. Sheldrick. SHELX-86. Program for crystal structure solution. University of Göttingen, Federal Republic of Germany, 1986) programs.

Figure 3:
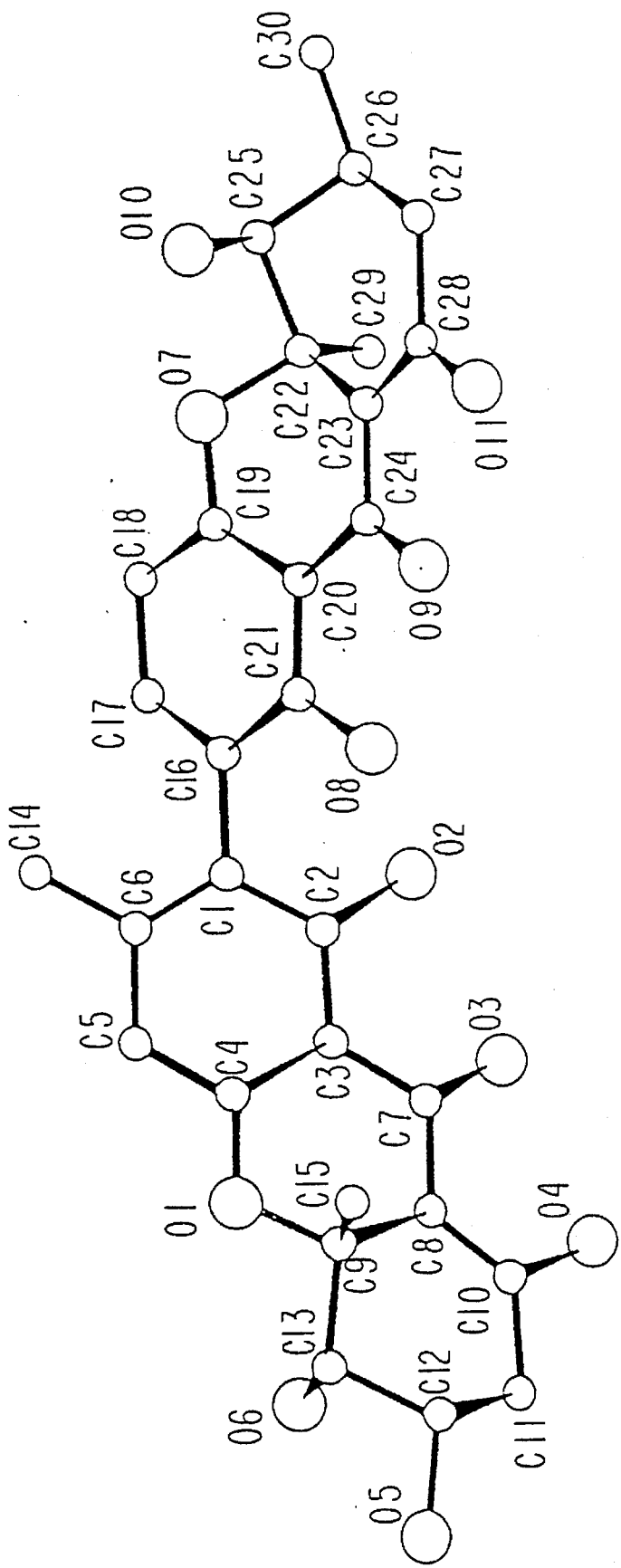

A summary of data is given in Table 1, and the resultant atomic coordinates are listed in Table 2. Bond lengths are given in Table 3 and the molecular structure is depicted in FIG. 3.

The number of observed reflections was too low for inclusion of H atoms, and only isotropic thermal parameters were used for C and O atoms.

TABLE 1

Crystal data and experimental conditions

| | |
|---|---|
| Molecular formula | $C_{30}H_{30}O_{11}$ |
| $M_r$ | 566.5604 |
| Crystal system | Orthorhombic |
| Space group | $P2_1 2_1 2_1$ |
| a | 6.456(2) Å |
| b | 16.791(8) Å |
| c | 23.734(5) Å |
| V | 2572 Å$^3$ |
| Z | 4 |
| $D_x$ | 1.457 g · cm$^{-3}$ |
| F(000) | 1184 |
| Temperature | 122 K. (−151° C.) |
| Crystal size | 0.20 · 0.10 · 0.05 mm |
| Min. h · k · l | 0 · 0 · 0 |

TABLE 1-continued

Crystal data and experimental conditions

| | |
|---|---|
| Max. h · k · l | 7 · 20 · 28 |
| Measured reflections | 2647 |
| Unique, observed refl. | 899 |
| Parameters | 165 |
| R(F) | 0.068 |
| wR(F) | 0.084 |

TABLE 2

Atomic coordinates and isotropic thermal parameters

| ATOM | X/A | Y/B | Z/C | Pop. | U |
|---|---|---|---|---|---|
| C1 | −0.0455 | 0.7231 | 0.3877 | 1.0000 | 0.0167 |
|    | 0.0030 | 0.0009 | 0.0007 | 0.0000 | 0.0045 |
| C2 | 0.1253 | 0.6785 | 0.3709 | 1.0000 | 0.0118 |
|    | 0.0027 | 0.0009 | 0.0006 | 0.0000 | 0.0041 |
| C3 | 0.1729 | 0.6051 | 0.3963 | 1.0000 | 0.0131 |
|    | 0.0028 | 0.0009 | 0.0006 | 0.0000 | 0.0041 |
| C4 | 0.0296 | 0.5750 | 0.4368 | 1.0000 | 0.0152 |
|    | 0.0031 | 0.0010 | 0.0006 | 0.0000 | 0.0044 |
| C5 | −0.1502 | 0.6149 | 0.4527 | 1.0000 | 0.0110 |
|    | 0.0027 | 0.0009 | 0.0006 | 0.0000 | 0.0039 |
| C6 | −0.1791 | 0.6927 | 0.4288 | 1.0000 | 0.0200 |
|    | 0.0029 | 0.0010 | 0.0007 | 0.0000 | 0.0045 |
| C7 | 0.3528 | 0.5588 | 0.3817 | 1.0000 | 0.0126 |
|    | 0.0028 | 0.0010 | 0.0006 | 0.0000 | 0.0040 |
| C8 | 0.4045 | 0.4924 | 0.4173 | 1.0000 | 0.0107 |
|    | 0.0025 | 0.0010 | 0.0006 | 0.0000 | 0.0039 |
| C9 | 0.2793 | 0.4862 | 0.4720 | 1.0000 | 0.0212 |
|    | 0.0029 | 0.0010 | 0.0007 | 0.0000 | 0.0046 |
| C10 | 0.5639 | 0.4423 | 0.4073 | 1.0000 | 0.0218 |
|    | 0.0030 | 0.0010 | 0.0007 | 0.0000 | 0.0046 |
| C11 | 0.6273 | 0.3726 | 0.4426 | 1.0000 | 0.0207 |
|    | 0.0029 | 0.0010 | 0.0007 | 0.0000 | 0.0048 |
| C12 | 0.5178 | 0.3775 | 0.4999 | 1.0000 | 0.0211 |
|    | 0.0030 | 0.0010 | 0.0007 | 0.0000 | 0.0047 |
| C13 | 0.2891 | 0.4000 | 0.4950 | 1.0000 | 0.0193 |
|    | 0.0030 | 0.0010 | 0.0007 | 0.0000 | 0.0047 |
| C14 | −0.3613 | 0.7385 | 0.4511 | 1.0000 | 0.0142 |
|    | 0.0028 | 0.0009 | 0.0006 | 0.0000 | 0.0041 |
| C15 | 0.3573 | 0.5446 | 0.5182 | 1.0000 | 0.0111 |
|    | 0.0026 | 0.0009 | 0.0006 | 0.0000 | 0.0040 |
| C16 | −0.0764 | 0.8059 | 0.3668 | 1.0000 | 0.0112 |
|    | 0.0027 | 0.0009 | 0.0006 | 0.0000 | 0.0039 |
| C17 | −0.2580 | 0.8304 | 0.3401 | 1.0000 | 0.0166 |
|    | 0.0029 | 0.0010 | 0.0007 | 0.0000 | 0.0042 |
| C18 | −0.2948 | 0.9108 | 0.3225 | 1.0000 | 0.0156 |
|    | 0.0030 | 0.0010 | 0.0007 | 0.0000 | 0.0042 |
| C19 | −0.1371 | 0.9650 | 0.3306 | 1.0000 | 0.0182 |
|    | 0.0029 | 0.0010 | 0.0007 | 0.0000 | 0.0045 |
| C20 | 0.0589 | 0.9434 | 0.3562 | 1.0000 | 0.0117 |
|    | 0.0027 | 0.0010 | 0.0006 | 0.0000 | 0.0040 |
| C21 | 0.0779 | 0.8638 | 0.3746 | 1.0000 | 0.0199 |
|    | 0.0031 | 0.0010 | 0.0007 | 0.0000 | 0.0045 |
| C22 | 0.0007 | 1.0944 | 0.3028 | 1.0000 | 0.0195 |
|    | 0.0028 | 0.0010 | 0.0007 | 0.0000 | 0.0046 |
| C23 | 0.1784 | 1.0822 | 0.3446 | 1.0000 | 0.0105 |
|    | 0.0029 | 0.0009 | 0.0006 | 0.0000 | 0.0040 |
| C24 | 0.2059 | 1.0036 | 0.3681 | 1.0000 | 0.0197 |
|    | 0.0028 | 0.0011 | 0.0007 | 0.0000 | 0.0042 |
| C25 | −0.0823 | 1.1806 | 0.3070 | 1.0000 | 0.0214 |
|    | 0.0030 | 0.0010 | 0.0007 | 0.0000 | 0.0044 |
| C26 | 0.0928 | 1.2378 | 0.2953 | 1.0000 | 0.0263 |
|    | 0.0031 | 0.0010 | 0.0007 | 0.0000 | 0.0051 |
| C27 | 0.2772 | 1.2286 | 0.3393 | 1.0000 | 0.0222 |
|    | 0.0030 | 0.0010 | 0.0007 | 0.0000 | 0.0046 |
| C28 | 0.3057 | 1.1423 | 0.3588 | 1.0000 | 0.0127 |
|    | 0.0029 | 0.0009 | 0.0007 | 0.0000 | 0.0041 |
| C29 | 0.0648 | 1.0695 | 0.2431 | 1.0000 | 0.0172 |
|    | 0.0030 | 0.0010 | 0.0007 | 0.0000 | 0.0045 |
| C30 | 0.0195 | 1.3230 | 0.2975 | 1.0000 | 0.0270 |
|    | 0.0031 | 0.0011 | 0.0007 | 0.0000 | 0.0050 |
| O1 | 0.0619 | 0.5028 | 0.4613 | 1.0000 | 0.0118 |

TABLE 2-continued

Atomic coordinates and isotropic thermal parameters

| ATOM | X/A | Y/B | Z/C | Pop. | U |
|---|---|---|---|---|---|
|  | 0.0017 | 0.0006 | 0.0004 | 0.0000 | 0.0027 |
| O2 | 0.2515 | 0.7062 | 0.3294 | 1.0000 | 0.0224 |
|  | 0.0019 | 0.0007 | 0.0004 | 0.0000 | 0.0031 |
| O3 | 0.4597 | 0.5757 | 0.3394 | 1.0000 | 0.0180 |
|  | 0.0019 | 0.0006 | 0.0004 | 0.0000 | 0.0029 |
| O4 | 0.6806 | 0.4527 | 0.3611 | 1.0000 | 0.0254 |
|  | 0.0020 | 0.0007 | 0.0005 | 0.0000 | 0.0030 |
| O5 | 0.5233 | 0.2963 | 0.5242 | 1.0000 | 0.0249 |
|  | 0.0019 | 0.0007 | 0.0004 | 0.0000 | 0.0032 |
| O6 | 0.1830 | 0.3493 | 0.4571 | 1.0000 | 0.0195 |
|  | 0.0019 | 0.0006 | 0.0004 | 0.0000 | 0.0029 |
| O7 | −0.1763 | 1.0430 | 0.3190 | 1.0000 | 0.0206 |
|  | 0.0019 | 0.0007 | 0.0004 | 0.0000 | 0.0029 |
| O8 | 0.2561 | 0.8428 | 0.4039 | 1.0000 | 0.0214 |
|  | 0.0020 | 0.0007 | 0.0005 | 0.0000 | 0.0030 |
| O9 | 0.3612 | 0.9905 | 0.4011 | 1.0000 | 0.0212 |
|  | 0.0018 | 0.0007 | 0.0004 | 0.0000 | 0.0030 |
| O10 | 0.4639 | 1.1313 | 0.3934 | 1.0000 | 0.0242 |
|  | 0.0020 | 0.0007 | 0.0005 | 0.0000 | 0.0032 |
| O11 | −0.1528 | 1.1941 | 0.3640 | 1.0000 | 0.0202 |
|  | 0.0019 | 0.0006 | 0.0004 | 0.0000 | 0.0030 |

TABLE 3

Bond lengths and angles

| C2 ---C1 | 1.391 ( 0.023 ) |
|---|---|
| C6 ---C1 | 1.399 ( 0.023 ) |
| C6 -C1 -C2 | 119.5 ( 1.4 ) |
| C16 ---C1 | 1.489 ( 0.022 ) |
| C16 -C1 -C2 | 120.8 ( 1.6 ) |
| C16 -C1 -C6 | 119.4 ( 1.6 ) |
| C3 ---C2 | 1.407 ( 0.021 ) |
| C3 -C2 -C1 | 121.4 ( 1.5 ) |
| O2 ---C2 | 1.360 ( 0.018 ) |
| O2 -C2 -C1 | 120.0 ( 1.4 ) |
| O2 -C2 -C3 | 118.7 ( 1.5 ) |
| C4 ---C3 | 1.426 ( 0.024 ) |
| C4 -C3 -C2 | 117.2 ( 1.6 ) |
| C7 ---C3 | 1.440 ( 0.023 ) |
| C7 -C3 -C2 | 123.0 ( 1.5 ) |
| C7 -C3 -C4 | 119.7 ( 1.4 ) |
| C5 ---C4 | 1.392 ( 0.023 ) |
| C5 -C4 -C3 | 123.6 ( 1.5 ) |
| O1 ---C4 | 1.361 ( 0.018 ) |
| O1 -C4 -C3 | 120.2 ( 1.6 ) |
| O1 -C4 -C5 | 116.2 ( 1.5 ) |
| C6 ---C5 | 1.435 ( 0.022 ) |
| C6 -C5 -C4 | 116.0 ( 1.5 ) |
| C5 -C6 -C1 | 121.8 ( 1.6 ) |
| C14 ---C6 | 1.502 ( 0.023 ) |
| C14 -C6 -C1 | 122.8 ( 1.5 ) |
| C14 -C6 -C5 | 115.4 ( 1.5 ) |
| C8 ---C7 | 1.439 ( 0.021 ) |
| C8 -C7 -C3 | 117.6 ( 1.5 ) |
| O3 ---C7 | 1.249 ( 0.018 ) |
| O3 -C7 -C3 | 121.1 ( 1.5 ) |
| O3 -C7 -C8 | 121.3 ( 1.6 ) |
| C9 ---C8 | 1.532 ( 0.022 ) |
| C9 -C8 -C7 | 115.3 ( 1.5 ) |
| C10 ---C8 | 1.351 ( 0.022 ) |
| C10 -C8 -C7 | 123.8 ( 1.5 ) |
| C10 -C8 -C9 | 120.6 ( 1.5 ) |
| C13 ---C9 | 1.549 ( 0.022 ) |
| C13 -C9 -C8 | 109.9 ( 1.4 ) |
| C15 ---C9 | 1.555 ( 0.021 ) |
| C15 -C9 -C8 | 112.6 ( 1.4 ) |
| C15 -C9 -C13 | 109.1 ( 1.3 ) |
| O1 ---C9 | 1.453 ( 0.021 ) |
| O1 -C9 -C8 | 110.4 ( 1.3 ) |
| O1 -C9 -C13 | 106.3 ( 1.4 ) |
| O1 -C9 -C15 | 108.4 ( 1.3 ) |
| C11 ---C10 | 1.495 ( 0.023 ) |

TABLE 3-continued

Bond lengths and angles

| C11 -C10 | 126.7 ( 1.6 ) |
|---|---|
| O4 ---C10 | 1.343 ( 0.019 ) |
| O4 -C10 -C | 119.3 ( 1.5 ) |
| O4 -C10 -C | 114.0 ( 1.6 ) |
| C12 ---C11 | 1.536 ( 0.025 ) |
| C12 -C11-C10 | 109.2 ( 1.5 ) |
| C13 ---C12 | 1.529 ( 0.026 ) |
| C13 -C12-C11 | 112.9 ( 1.4 ) |
| O5 ---C12 | 1.480 ( 0.020 ) |
| O5 -C12 -C11 | 106.6 ( 1.4 ) |
| O5 -C12 -C13 | 106.3 ( 1.4 ) |
| C12 -C13 -C9 | 107.3 ( 1.5 ) |
| O6 ---C13 | 1.415 ( 0.019 ) |
| O6 -C13 -C9 | 108.5 ( 1.3 ) |
| O6 -C13 -C12 | 111.6 ( 1.4 ) |
| C17 ---C16 | 1.395 ( 0.023 ) |
| C17 -C16-C1 | 122.7 ( 1.6 ) |
| C21 ---C16 | 1.405 ( 0.022 ) |
| C21 -C16 -C1 | 120.5 ( 1.6 ) |
| C21 -C16 -C16 | 116.8 ( 1.5 ) |
| C18 ---C17 | 1.433 ( 0.022 ) |
| C18 -C17-C16 | 123.4 ( 1.7 ) |
| C19 ---C18 | 1.379 ( 0.024 ) |
| C19 -C18-C17 | 117.3 ( 1.7 ) |
| C20 ---C19 | 1.449 ( 0.023 ) |
| C20 -C19-C18 | 122.5 ( 1.5 ) |
| O7 ---C19 | 1.362 ( 0.018 ) |
| O7 -C19 -C18 | 118.0 ( 1.6 ) |
| O7 -C19 -C20 | 119.2 ( 1.5 ) |
| C21 ---C20 | 1.412 ( 0.022 ) |
| C21 -C20-C19 | 116.3 ( 1.6 ) |
| C24 ---C20 | 1.414 ( 0.023 ) |
| C24 -C20-C19 | 119.4 ( 1.5 ) |
| C24 -C20-C21 | 123.8 ( 1.6 ) |
| C20 -C21-C16 | 123.6 ( 1.7 ) |
| O8 ---C21 | 1.389 ( 0.021 ) |
| O8 -C21 -C16 | 118.5 ( 1.4 ) |
| O8 -C21 -C20 | 117.9 ( 1.6 ) |
| C23 ---C22 | 1.531 ( 0.023 ) |
| C25 ---C22 | 1.546 ( 0.022 ) |
| C25 -C22-C23 | 110.1 ( 1.3 ) |
| C29 ---C2 | 1.535 ( 0.023 ) |
| C29 -C22-C23 | 111.1 ( 1.4 ) |
| C29 -C22-C25 | 114.1 ( 1.3 ) |
| O7 ---C22 | 1.482 ( 0.020 ) |
| O7 -C22-C23 | 109.4 ( 1.2 ) |
| O7 -C22-C25 | 105.1 ( 1.3 ) |
| O7 -C22 -C29 | 106.7 ( 1.3 ) |
| C24 ---C223 | 1.444 ( 0.022 ) |
| C24 -C23-C22 | 117.6 ( 1.5 ) |
| C28 ---C23 | 1.343 ( 0.021 ) |
| C28 -C23-C22 | 121.4 ( 1.4 ) |
| C28 -C23-C24 | 121.0 ( 1.5 ) |
| C23 -C24-C20 | 119.6 ( 1.6 ) |
| O9 ---C24 | 1.291 ( 0.019 ) |
| O9 -C24-C20 | 121.4 ( 1.5 ) |
| O9 -C24-C23 | 119.0 ( 1.6 ) |
| C26 ---C25 | 1.509 ( 0.024 ) |
| C26 -C25-C22 | 108.9 ( 1.5 ) |
| O11 ---C25 | 1.446 ( 0.018 ) |
| O11 -C25-C22 | 108.4 ( 1.3 ) |
| O11 -C25-C26 | 107.9 ( 1.4 ) |
| C27 ---C26 | 1.591 ( 0.024 ) |
| C27 -C26-C25 | 112.3 ( 1.4 ) |
| C30 ---C26 | 1.508 ( 0.024 ) |
| C30 -C26-C25 | 111.3 ( 1.6 ) |
| C30 -C26-C27 | 107.7 ( 1.5 ) |
| C28 ---C27 | 1.533 ( 0.021 ) |
| C28 -C27-C26 | 112.3 ( 1.5 ) |
| C27 -C28-C23 | 124.1 ( 1.6 ) |
| O10 ---C28 | 1.323 ( 0.020 ) |
| O10 -C28-C23 | 121.5 ( 1.4 ) |
| O10 -C28-C27 | 114.3 ( 1.5 ) |
| C9 -O1 -C4 | 113.2 ( 1.3 ) |
| C22 -O7 -C19 | 118.0 ( 1.4 ) |

NMR-Spectroscopy $^1$H NMR and $^{13}$C NMR spectra for the isolate were established in relation to tetramethylsilane (TMS) by dissolving the crystals in tetrahydrofuran$_8$ (THF-d$_8$) and using a Bruker WM 400 instrument at magnetic field strengths of 400 MHz and 100.6 MHz, respectively.

The spectra are listed below:

$^1$H-NMR, 400 MHz (THF-d$_8$)

δ: 1.15 (d, 3H), 1.45 (s, 3H), 1.5 (s, 3H),2.05 (s, 3H) 2.2 (m, 1H), 2.3 (dd, 1H), 2.45 (dd, 1H), 2.55 (dd, 1H), 2.7 (dd, 1H), 3.75 (s, 1H), 3.95 (s, 1H), 4.0 (m, 1H), 4.1 (s, 1H), 4.3 (s, 1H), 4.7 (s, 1H), 6.3 (s, 1H), 6.45 (d, 1H), 7.2 (d, 1H), 11.7 (s, 1H), 11.85 (s, 1H), 13.75 (s, 1H), 13.85 (s, 1H).

$^{13}$C-NMR, 100.6 MHz (THF-d$_8$)

δ: 18.3, 21.2, 25.9, 26.2, 29.9, 33.8, 35.6, 65.9, 75.2, 75.9, 82.1, 83.2, 105.3, 105.4, 105.5, 107.5, 108.5, 109.8, 117.5, 118.7, 141.2, 150.0, 158.4, 159.3, 160.9, 161.1, 176.0, 178.4, 188.8, 189.3.

Mass Spectroscopy

Electron impact (EI) mass spectrum was performed at 70 eV on a VG 70–250 SQ spectrometer with direct insertion via an insertion probe heated from 30° C. to 300° C. in 100° C./min. The scanning speed was 10 s/decade in the range 80 to 800 Dalton, and the resolution was 3300.

| Exact mass: | |
|---|---|
| measured | 566.1786 |
| calculated for C$_{30}$H$_{30}$O$_{11}$ | 566.1788. |
| MS m/z (%): | 566 (100), 548 (35), 530 (22), 500 (42), 472 (25), 407 (17). |

Mammalian Pathogenicity

Culture broth containing the BK210 and viable spores and mycelium showed no effect on mice, intraperitoneally applied at the rate of 20 ml per kg body weight. The broth contained approximately 1×10$^7$ viable counts/ml.

Anti-EPI Activity of BK201

A. Materials and Methods

1. Preparation of anti-EPI antibodies: Recombinant human EPI(rEPI) was obtained rom transfected BHK cells as described by Pedersen et al. (j. Biol. Chem. 265: 6786, 1990). rEPI was purified by heparin affinity chromatography, ion exchange and reversed phase chromatography (Nordfang et al., Biotech Plasma Prot.p. 98, 1990). rEPI obtained in this way was pure judged from SDS-PAGE. Rabbits were immunized on day 0, 14, and 35 followed by 21 day intervals. Each immunization was with 0.1 mg of rEPI in adjuvant. The first immunization as with Freunds complete adjuvant while the next immunization was with Freunds incomplete adjuvant. The antisera obtained were tested for inhibition of EPI activity in an EPI activity assay, described below. The inhibition was quantitated like FVIII inhibiting antibodies in a Bethesda assay: equal volumes of diluted antiserum and EPI(1 U/ml) ere incubated for 2 hours at 37° C. EPI activity was measured and the dilution of antiserum that inhibits the activity by 50% gives the titer. The rabbit antisera had inhibiting titers between 1000 and 4000 "Bethesda-like" units/ml towards both rEPI and human plasma EPI. Below 50-fold dilution serum from unimmunized rabbits did not influence the activity of the EPI sample(1 U/ml). IgG was purified from the antisera by anion exchange chromatography. The IgG preparation with 8 mg IgG/ml contained 2000 "Bethesda-like" inhibiting units/ml towards human plasma EPI.

2. Assay for EPI activity: EPI was measured in a chromogenic microplate assay, modified after the method of Sandset et al. (Thromb. Res. 47: 389, 1989). Heat treated plasma pool was used as a standard. This standard is set to contain 1 U/ml of EPI activity. Standards and samples were diluted in buffer A (0.05M tris/0.1M NaCl/0.1M Na-citrate/0.02% NaN$_3$/pH 8.0) containing 1 µg/ml polybrene and 0.2% bovine serum albumin. FVIIa/TF/FX/CaCl$_2$ combination reagent was prepared in buffer A and contained 1.6 ng/FVIIa(Novo Nordisk A/S), human tissue factor diluted 60-fold(Hjort, Scand. J. Clin. Lab. Invest. 9: 1957), 50 ng/ml FX (Sigma) and 18 mM CaCl$_2$. The assay was performed in microplate strips at 37° C. 50 µl of samples and standards were pipetted into the strips and 100 µl combination reagent was added to each well. After 10 minutes incubation, 50 µl of FX (3.2 µg/ml) was added to each well and after another 10 minutes 25 µl of chromogenic substrate for FXa(S2222) was added 10 minutes after the addition of substrate. The reaction was stopped by addition of 50 µl 1.0M citric acid pH 3.0. The microplate was read at 405 nm.

3. Coagulation assay: Coagulation activity was measured using an ACL coagulation apparatus. 20 µl of antibody solution or EPI solution was incubated with 200 µl plasma for 15 minutes at room temperature. After preheating to 37° C. the ACL mixes 75 µl of plasma sample with 75 µl of diluted TF in 20 mM CaCl$_2$. 50 mM NaCL, 17 mM imidazole, 33 µg/ml BSA, pH 7.4.

B. Results

The compound described above is tested in each of the TFPI(EPI) inhibitor and coagulation assays. When tested in the EPI inhibitor assay, the titer of the pure compound toward human plasma EPI is 80 "Bethesda-like" units/mmol.

When added to normal human plasma, the dilute TF-induced coagulation time is reduced to the level of the effect of anti-TFPI antibodies(goat or rabbit) at a concentration of 150 µM, while the compound had no effect on TFPI-deficient plasma (neutralized with rabbit anti-TFPI antibodies). These results are presented in FIG. 1.

When added to normal rabbit plasma and FVIII deficient plasma (neutralized with goat anti-FVIII antibodies), the dilute TF-induced coagulation time was reduced to the level of effect of anti-TFPI antibodies (goat) at a concentration of 300 µM, as shown in FIG. 2.

Thus, the results show that the Ascochyta compound is useful as a TFPI inhibitor having activity qualitatively equivalent with anti-TFPI antibodies in reducing coagulation time.

What we claim is:

1. A method of decreasing prolonged coagulation time in a mammal comprising administering to the mammal an effective amount of a compound of the general formula Ia

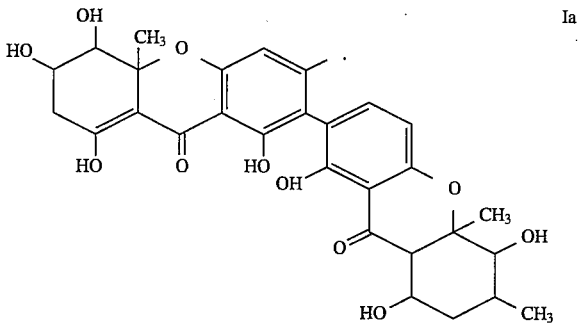

2. The method of claim 1 in which the prolonged coagulation time is associated with a medical condition selected from the group consisting of hemophilia A, hemophilia B, idiopathic thrombocytopenia, surgical procedures, or disseminated intravascular coagulation.

* * * * *